US008158397B2

(12) United States Patent
Jones et al.

(10) Patent No.: US 8,158,397 B2
(45) Date of Patent: Apr. 17, 2012

(54) BACILLUS 029CEL CELLULASE

(75) Inventors: Brian E. Jones, Leiden (NL); William D. Grant, Leicestershire (GB); Shaun Heaphy, Leicester (GB); Susan Grant, Leicestershire (GB)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 12/543,247

(22) Filed: Aug. 18, 2009

(65) Prior Publication Data

US 2010/0048417 A1 Feb. 25, 2010

Related U.S. Application Data

(63) Continuation of application No. 10/549,943, filed as application No. PCT/US2004/013258 on Apr. 28, 2004, now Pat. No. 7,604,974.

(60) Provisional application No. 60/466,831, filed on Apr. 29, 2003.

(51) Int. Cl.
| | |
|---|---|
| *C12P 7/06* | (2006.01) |
| *C12P 7/10* | (2006.01) |
| *C12P 19/02* | (2006.01) |
| *C12N 9/42* | (2006.01) |
| *C07H 21/04* | (2006.01) |

(52) U.S. Cl. ........ 435/161; 435/209; 435/320; 435/165; 435/105; 536/23.2

(58) Field of Classification Search ........................ None
See application file for complete search history.

(56) References Cited

U.S. PATENT DOCUMENTS

| | | | |
|---|---|---|---|
| 4,338,397 A | 7/1982 | Gilbert et al. | |
| 4,411,994 A | 10/1983 | Gilbert et al. | |
| 4,513,085 A | 4/1985 | Nakatsukasa et al. | |
| 4,513,086 A | 4/1985 | Fayerman et al. | |
| 4,738,682 A | 4/1988 | Boegh et al. | |
| 4,745,056 A | 5/1988 | Guterman et al. | |
| 5,254,283 A | 10/1993 | Arnold et al. | |
| 5,264,366 A | 11/1993 | Ferrari et al. | |
| 5,364,770 A | 11/1994 | Berka et al. | |
| 5,514,590 A | 5/1996 | Garvin et al. | |
| 5,622,866 A | 4/1997 | Motamedi et al. | |
| 6,255,115 B1 | 7/2001 | Beijersbergen et al. | |
| 6,566,112 B2 | 5/2003 | Jones et al. | |

FOREIGN PATENT DOCUMENTS

| | | |
|---|---|---|
| EP | 0 220 016 A2 | 4/1987 |
| EP | 0 273 125 A2 | 7/1988 |
| EP | 0 684 304 A2 | 11/1995 |
| FI | 87372 B | 9/1992 |
| GB | 1 368 599 A | 10/1974 |
| GB | 2 094 826 A | 9/1982 |
| GB | 2 095 275 A | 9/1982 |
| JP | 03-251174 A2 | 11/1991 |
| WO | WO 88/07079 A1 | 9/1988 |
| WO | WO 95/16360 A1 | 6/1995 |
| WO | WO 99/31255 A2 | 6/1999 |
| WO | WO 03/106654 A2 | 12/2003 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Ahsan, M.M. et al. "Cloning, DNA sequencing, and expression of the gene encoding *Clostridium thermocellum* cellulase CelJ, the largest catalytic component of the cellulosome." *J. Bacteriol.* 178(19):5732-5740, 1996.
Altschul, S.F. et al. "Basic local alignment search tool." *J. Mol. Biol* 215(3):403-410, 1990.
Altschul, S.F. et al. "Gapped BLAST and PSI—BLAST: a new generation of protein database search programs." *Nucleic Acids Res.* 25:3389-3402, 1997.
Bajar, A. et al. "Identification of a fungal cutinase promoter that is inducible by a plant signal via a phosphorylated trans-acting factor." *PNAS* 88(18):8208-8212, 1991.
Brigidi, P. et al. "Genetic transformation of intact cells of *Bacillus subtilis* by electroporation." *FEMS Microbiology Letters* 67(1-2):135-138, 1990.
Database Genbank. "*Thermomonospora fusca* beta-1,4-endoglucanase precursor (EI) gene, complete cds." Accession No. L20094, 1998.
Davies, G.J. et al. "Structure of the *Bacillus* agaradherans Family 5 Endoglucanase at 1.6 Å and Its Cellobiose Complex at 2.0 Å Resolution." *Biochemistry* 37(7):1926-1932, 1998.
Evan, G.I. et al. "Isolation of monoclonal antibodies specific for human c-myc proto-oncogene product." *Molecular and Cellular Biology* 5(12):3610-3616, 1985.
Field, J. et al. "Purification of a RAS-responsive adenylyl cyclase complex from *Saccharomyces cerevisiae* by use of an epitope addition method." *Molecular and Cellular Biology* 8(5):2159-2165, 1988.
Filho, E.X.F. "Purification and characterization of a beta-glucosidase from solid-state cultures of *Humicola grisea* var. thermoidea." *Canadian Journal of Microbiology* 42(1):1-5, 1996.
Freer, S.N. "Kinetic characterization of a beta-glucosidase from a yeast, *Candida wickerhamii*.." *Journal of Biological Chemistry* 268(13):9337-9342, 1993.
Ghauri, M.A. et al. "Phylogenetic analysis of different isolates of *Sulfobacillus* spp. isolated from uranium-rich environments and recovery of genes using integron-specific primers." *Extremophiles* 7(5):341-345, 2003.
Gillam, S. et al. "Site-specific mutagenesis using synthetic oligodeoxyribonucleotide primers: I. Optimum conditions and minimum oligodeoxyribonucleotide length." *Gene* 8(1):81-97, 1979.
Godbole, S. et al. "Cloning and expression of *Trichoderma reesei* cellobiohydrolase I in *Pichia pastoris*." *Biotechnology Progress* 15(5):828-833, 1999.

(Continued)

*Primary Examiner* — Anand Desai
*Assistant Examiner* — Iqbal H Chowdhury
(74) *Attorney, Agent, or Firm* — Danisco US Inc.

(57) ABSTRACT

The present invention provides a novel cellulase nucleic acid sequence, designated 029cel, and the corresponding 029cel amino acid sequence. The invention also provides expression vectors and host cells comprising a nucleic acid sequence encoding 029cel, recombinant 029cel proteins and methods for producing the same.

4 Claims, 4 Drawing Sheets

OTHER PUBLICATIONS

Goldman, G. H. et al. "Transformation of *Trichoderma harzianum* by high-voltage electric pulse." *Current Genetics* 17(2):169-174, 1990.

Grant, W.D. et al. "The isolation of alkalophilic bacteria." In *Microbial Growth and Survival in Extremes of Environment*, eds. G.W. Gould et al. New York: Academic Press, pp. 27-36, 1980.

Hari Krishna, S. et al. "Simultaneous saccharification and fermentation of lignocellulosic wastes to ethanol using a thermotolerant yeast." *Bioresource Technology* 77(2):193-196, 2001.

Hopp, T.P. et al. "A Short Polypeptide Marker Sequence Useful for Recombinant Protein Identification and Purification." *Nat Biotech* 6(10):1204-1210, 1988.

Juhász, T. et al. "Effect of pH on cellulase production of *Trichoderma ressei* RUT C30." *Applied Biochemistry and Biotechnology* 113(1):201-211, 2004.

Jung, E.D. et al. "DNA sequences and expression in *Streptomyces lividans* of an exoglucanase gene and an endoglucanase gene from *Thermomonospora fusca*.." *Appl. Environ. Microbiol.* 59(9):3032-3043, 1993.

Knowles, J. et al. "Cellulase families and their genes." *Trends in Biotechnology* 5(9):255-261, 1987.

Lee, C.C. et al. "Cloning and characterization of two cellulase genes from *Lentinula edodes*." *FEMS Microbiology Letters* 205(2):355-360, 2001.

Lomovskaya, N.D. et al. "Characterization of Temperate Actinophage φC31 Isolated from *Streptomyces coelicolor* A3(2)." *J. Virol.* 9(2):258-262, 1972.

Lorito, M. et al. "Biolistic transformation of *Trichoderma harzianum* and *Gliocladium virens* using plasmid and genomic DNA." *Current Genetics* 24(4):349-356, 1993.

Lutz-Freyermuth, C. et al. "Quantitative determination that one of two potential RNA-binding domains of the A protein component of the U1 small nuclear ribonucleoprotein complex binds with high affinity to stem-loop II of U1 RNA." *Proc. Natl. Acad. Sci. U.S.A* 87(16):6393-6397.

Martin, G.A. et al. "GAP domains responsible for ras p21-dependent inhibition of muscarinic atrial K+ channel currents." *Science* 255(5041):192-194, 1992.

Mielenz, Jonathan R. "Ethanol production from biomass: technology and commercialization status." *Current Opinion in Microbiology* 4(3):324-329, 2001.

Nevalainen, H. et al. "Molecular biology of cellulolytic fungi." In the Mycota II, *Genetics and Biotechnology*, ed. U. Kück. Berlin, Germany: Springer-Verlag, pp. 303-319, 1995.

Ohmiya, K. et al. "Structure of cellulases and their applications." *Biotechnology & Genetic Engineering Reviews* 14:365-414, 1997.

Paborsky, L.R. et al. "Mammalian cell transient expression of tissue factor for the production of antigen." *Protein Eng.* 3(6):547-553, 1990.

Penttilä, M. et al. "A versatile transformation system for the cellulolytic filamentous fungus *Trichoderma reesei*." *Gene* 61(2):155-64, 1987.

Roberts, S. et al. "Generation of an antibody with enhanced affinity and specificity for its antigen by protein engineering." *Nature* 328(6132):731-734, 1987.

Schneider, E. et al. "Functional Purification of a Bacterial ATP-Binding Cassette Transporter Protein (MalK) from the Cytoplasmic Fraction of an Overproducing Strain." *Protein Expression and Purification* 6(1):10-14, 1995.

Schulein, M. "Cellulases of *Trichoderma reesei*." *Methods in enzymology* 160:234-242, 1988.

Shirai, T. et al. "Crystal structure of alkaline cellulase K: insight into the alkaline adaptation of an industrial enzyme." *Journal of Molecular Biology* 310(5):1079-1087, 2001.

Shoemaker, S.P. et al. "Enzymic activities of endo-1,4-beta-D-glucanases purified from *Trichoderma viride*." *Biochimica et Biophysica Acta (BBA)—Enzymology* 523(1):133-146, 1978.

Skinner, R.H. et al. "Use of the Glu-Glu-Phe C-terminal epitope for rapid purification of the catalytic domain of normal and mutant ras GTPase-activating proteins." *J. Biol. Chem.* 266(22):14163-14166, 1991.

Suurnäkki, A. et al. "*Trichoderma reesei* cellulases and their core domains in the hydrolysis and modification of chemical pulp." *Cellulose* 7(2):189-209, 2000.

Teather, R.M. et al. "Use of Congo red-polysaccharide interactions in enumeration and characterization of cellulolytic bacteria from the bovine rumen.." *Appl. Environ. Microbiol.* 43(4):777-780, 1982.

Te'o, V.S.J. et al. "Codon optimization of xylanase gene xynB from the thermophilic bacterium *Dictyoglomus thermophilum* for expression in the filamentous fungus *Trichoderma reesei*." *FEMS Microbiology Letters* 190(1):13-19, 2000.

Tholudur, A. et al. "Mathematical modeling and optimization of cellulase protein production using *Trichoderma reesei* RL-P37." *Biotechnology and Bioengineering* 66(1):1-16, 1999.

Wood, T.M. "Properties of cellulolytic enzyme systems." *Biochemical Society Transactions* 13(2):407-410, 1985.

Yelton, M.M. et al. "Transformation of *Aspergillus nidulans* by using a trpC plasmid." *Proc. Natl. Acad. Sci. U.S.A* 81(5):1470-4, 1984.

International Search Report and Written Opinion of the International Searching Authority for International Application No. PCT/USUS04/13258 dated Jul. 1, 2008.

* cited by examiner

Figure 1A   Nucleotide sequence of inserted environmental DNA (029cel)
SEQ ID NO:1

| | | | | |
|---|---|---|---|---|
| ATCAACACGC | TGGAAAGTAA | TTTCAAGGGT | AAGGCCATCG | GTTGCCGCCG | 50
| GGGTAGAAAT | GTGCGGTTGG | ATTTCGTTGA | GCGGCGTCGC | CGGCGTTCCA | 100
| CCGAGGGCAT | AGCGCAGCAG | GTTGGCGATG | CCACCGGTGA | GGCCTTCGGG | 150
| GCCGCCTACG | ATGTTGTGCT | CAGCCGCCCA | TGCGATGTAG | CCGTCCGGCT | 200
| CGGGTTCGCT | CGCGGGGGTG | AAGAAGACAA | TGTCGTCGAG | ATAAAGGTTG | 250
| CCGCTTCCGC | TCTCAACGCC | GCCGAGGTTG | AATTGGATTT | CGCAAATTCT | 300
| CGTTAGGTCC | AGCACGGAAT | CGCCGACGAG | GTCGGCTATG | GGAATCTGAA | 350
| TGCGCCCATA | GGGTTGGGTA | CGCGGAAGGG | ACACGTAGGG | ACCCACTTTG | 400
| TCATTGGGCG | AGACGAGCCG | GACAAAGATT | TGGTGCGCCG | CCTGCGAGGG | 450
| GCCTTGGAGG | GCGAGAGAAA | GGTACGTGAG | GGCGCTGATG | TCGTGCGTGG | 500
| GACCGTCTCC | CCAGTTGTCG | AGATTGAGCC | CAAATCCGGC | CCACCATCCG | 550
| GCGATAGTGT | AGCTCCAATG | GTAGTGACGC | TCACCCTCGA | AGCCGCCGCT | 600
| GGAGAGTTCC | TGCAAGCCGT | CGCCCCAAAT | GCCCGTGATG | AGCGTTGCCT | 650
| CGTCACGGTA | GATCACAAGT | TCGGCGGCGG | GTGCCGGGGG | AAGATCGCCT | 700
| TGAGTGATCA | CGAGAGTGGC | GGTGGCGCTG | CCTTCGTGAT | TAGGGTCGGT | 750
| AATGGTGGCG | ACGACCGTGT | AGCTACCGGG | CCCCACTGGC | GCATGGGTGG | 800
| AACCGTTGTA | GGTAAAGGAG | ACGTCAAGCC | CCACGGGATG | GGTCTCGGCA | 850
| AGAGCGGCCT | TGGGGGTGCC | GTCGAAAACG | TGTTCCAAAT | TGGAGAGCGT | 900
| GATGGTGGCG | GGTGCCTTGA | GCACAGTCAC | AGAAACAGTG | GATTGCACGG | 950
| GATCGTGCGC | TGCCGTGTCT | GCAGGTGTGA | AGACCACGCT | GTAAAAACGG | 1000
| GTTCCGGCGG | ACGGTGCAAG | GCCGGACAGG | ACAAAGGCAA | AGTCGCCGGG | 1050
| GACGGCGGCT | ACTCCGCCGC | TCAGGCCGGC | CTCCGCAAGG | GTTTGCCCGA | 1100
| AGGTGATGGG | TGCGGCTGTG | GGCCACATCT | CCACAAGGCC | GGTGTCCCCC | 1150
| TCGTCACGCA | CCGGCATGAG | GGCGGAGAGG | AGATGAATGT | AACTGGCTTG | 1200
| GTAATTGATG | TCGGGCTCGG | TGATTTCCCA | TGAGTTCTCC | GGCCAAAAAC | 1250
| CATTCCAATC | AAGGTAGGCT | TTTTGCACGG | GTTGGTCTCG | GATCGCCTGA | 1300
| ATGCTTCCGC | TGTATTTGGG | CATTGGGACC | CGCCCGAAAG | AAAACCAGGA | 1350
| GCGGGACCGT | AGAGTGAAGT | GAGGGCATTG | TCCCAGTCCG | GCCATCGCGG | 1400
| AACCAATGGT | GGTAGATTTC | ATTGGCTGCA | CGGTCAGCGC | CGCTGGCATA | 1450
| CATGTTGCTA | AGATAGACCA | TGCCCATTGG | GTTCACTCCG | TGGAGATAGT | 1500
| GCAGGTAGCC | CATCGCGGCA | TCGCGATGCG | CGGCCGCGTC | GGCGGGGTTG | 1550
| AGCCCAAGCC | TCCGTACCCC | CTCGAAGAAA | AAGCCAGCCT | GAGACTTTGT | 1600
| TTTGTTCGAG | CCCCACGTGT | AATCCTGATC | CTTCAGGTAG | GCGCGGTAGG | 1650
| CGTCGGTCTG | GTTATTCCAT | GCACCGAGAA | ACTCCCCACC | GTTTATAGAA | 1700
| GCCGCCATCC | GGTTGCGGAT | GTCGGCAGAG | ACGCTAGGCG | TCGCTCCCGG | 1750
| GAGGGTCGTG | TAGTGGGCGA | GAGCTTTTTG | TAGCTCACCT | TGAAAGGGGA | 1800
| AGAAATACCA | CCACTGCACG | GGCTCCATAT | CGAGATAGCG | CACATCGAAG | 1850
| AAATCGCGAT | AGACCGCACC | GCCCGTGCGC | TCGAAGAGCA | TGGCGGCGGC | 1900
| CATCACACGG | TTGGCTAGCG | TATCGTGGGC | ATTGCGCGAG | GGGCTCACGG | 1950
| AAGCAAATCC | GGTGTTGTCG | AAAGGCACAT | GAGGATGGAC | CATGGTCCAA | 2000
| TTCCATGCGG | CGATGGCAGC | GGATTCGAGG | GTGACGGCAT | AATCGCTCAT | 2050
| GCCTACGCTC | TCAAAGACAG | TCGCCCCGAG | GGCGAAAGCG | GCGGCAGCCA | 2100
| TGGCAGTGGC | CTCGGTCGAG | ACGGGCCGT | AGTAACGCGG | ATGGGTGTCG | 2150
| GTGCTCGGCG | GGCTGGCGCT | CTGGTGCCCC | GTCACGGAAA | CTTTCCCGAG | 2200
| AATAGCCCCG | CTCGGCTCCT | GCATGCGTAA | GAGCCAGTCC | ATTCCCCATT | 2250
| TGACTTCGTC | AAGCAGGTCG | GGGACACCGT | TGCCGGATTC | CGGGATGCCA | 2300
| AAATCATCGG | TAAAGACGTC | AGGCCGCCCT | TGATAGGCAA | GGAGCAGCTC | 2350
| CAGGATGACG | CGCCCCGTCC | ACTCGCTGTA | CTTGTTGAAA | TCGCCCGCAT | 2400

Figure 1B

| | | | | | |
|---|---|---|---|---|---|
| CGAACCAACC | GCCGCTGAGA | TCGCGCTCCA | AGGAGGCATT | CCCCATATCC | 2450 |
| CAGATGGGGC | GGCTGGCGAC | GTCCTGCGGG | TGAGAAGCGG | CATCGGCCCA | 2500 |
| GTTCGCGTGG | GCGTAGGGCA | CCTCCTTGGC | AAACCCGGAG | CGCTGATAGA | 2550 |
| AGAACATGCG | CACGGCCTCG | CGCAGGACAA | CATCGTAAAC | ATCCGCGCCA | 2600 |
| ATGGCGAAAC | TATCGGAATG | AGTGTTGTTG | GCAGGATCGT | GGATGCGGTA | 2650 |
| GTGGCCGGGC | TCGGCAACTA | CCGTAAAATC | AAACCACCAC | ACGCGGTCTC | 2700 |
| CCGATTGAAT | ATGGATGGCG | CCGCCGTTCC | ACGGGACCGG | TGAGCCGGAG | 2750 |
| AAAACCACGA | CGCCATCGTT | CACGCGACGG | ACCTCCAGCG | TTGCGCCGGG | 2800 |
| GCTGTAGCTC | TCGGCGCTGT | TCCAGCCAAT | CTGCGGGTCG | GCGATCACCG | 2850 |
| CCACCTTGGT | GGCATCGGCG | GGTAACCGA | ATTGGTCGAT | GCGGATTTTA | 2900 |
| TCGGTGTGGG | TGGAGGCGAC | GAGGGCGGAG | CTGCCCATGA | GCAGCAAGAA | 2950 |
| AAAGCCCGCT | GTCGGCCCGA | TACCAAAAAA | ACGAATAGGG | AGAGAAAAAT | 3000 |
| TCATAGCAGG | ATGTGGATAC | GGAAGGGGG | AAAACGGTGC | AAAGACCCAA | 3050 |
| GCCCAACGCT | TGGCGAAAAC | TGGATGGTTG | GTTTATCAAG | AAAAGCGCTT | 3100 |
| TTGAGCCAAA | AGCTGCGGGC | AATCCTTATT | GCGTTTCACA | ATATTTTCAC | 3150 |
| ATCGTCGGCG | GCACGACTTT | TCGATGGGCG | ACTTGACAGC | GTATTCTCTC | 3200 |
| AGGCGCGAGG | CTGCAAACCT | TATGAAAAAA | GGCCCGCGCA | GCGATCTGTC | 3250 |
| CCCGGTCAAA | ATCCAGTCAA | GGTTTGTTCA | AGGGTTTGAG | GTCTGATAGA | 3300 |
| GGCACAGTCG | AGCCATCAGC | AGTCGCATTG | AGTAGGGTTG | TTGGAGAAAG | 3350 |
| TGTGCAAATG | ACCGCTGCCG | AAGGAACTGT | GGAGACAAAA | AGCATATTTT | 3400 |
| CCTCGCCAAG | | | | | 3410 |

Figure 2
The nucleotide sequence of 029cel ORF

| | | | | | |
|---|---|---|---|---|---|
| ATGAATTTTT | CTCTCCCTAT | TCGTTTTTTT | GGTATCGGGC | CGACAGCGGG | 50 |
| CTTTTTCTTG | CTGCTCATGG | GCAGCTCCGC | CCTCGTCGCC | TCCACCCACA | 100 |
| CCGATAAAAT | CCGCATCGAC | CAATTCGGTT | ACCCCGCCGA | TGCCACCAAG | 150 |
| GTGGCGGTGA | TCGCCGACCC | GCAGATTGGC | TGGAACAGCG | CCGAGAGCTA | 200 |
| CAGCCCCGGC | GCAACGCTGG | AGGTCCGTCG | CGTGAACGAT | GGCGTCGTGG | 250 |
| TTTTCTCCGG | CTCACCGGTC | CCGTGGAACG | GCGGCGCCAT | CCATATTCAA | 300 |
| TCGGGAGACC | GCGTGTGGTG | GTTTGATTTT | ACGGTAGTTG | CCGAGCCCGG | 350 |
| CCACTACCGC | ATCCACGATC | CTGCCAACAA | CACTCATTCC | GATAGTTTCG | 400 |
| CCATTGGCGC | GGATGTTTAC | GATGTTGTCC | TGCGCGAGGC | CGTGCGCATG | 450 |
| TTCTTCTATC | AGCGCTCCGG | GTTTGCCAAG | GAGGTGCCCT | ACGCCCACGC | 500 |
| GAACTGGGCC | GATGCCGCTT | CTCACCCGCA | GGACGTCGCC | AGCCGCCCCA | 550 |
| TCTGGGATAT | GGGGAATGCC | TCCTTGGAGC | GCGATCTCAG | CGGCGGTTGG | 600 |
| TTCGATGCGG | GCGATTTCAA | CAAGTACAGC | GAGTGGACGG | GGCGCGTCAT | 650 |
| CCTGGAGCTG | CTCCTTGCCT | ATCAAGGGCG | GCCTGACGTC | TTTACCGATG | 700 |
| ATTTTGGCAT | CCCGGAATCC | GGCAACGGTG | TCCCCGACCT | GCTTGACGAA | 750 |
| GTCAAATGGG | GAATGGACTG | GCTCTTACGC | ATGCAGGAGC | CGAGCGGGGC | 800 |
| TATTCTCGGG | AAAGTTTCCG | TGACGGGGCA | CCAGAGCGCC | AGCCCGCCGA | 850 |
| GCACCGACAC | CCATCCGCGT | TACTACGGCC | CCGTCTCGAC | CGAGGCCACT | 900 |
| GCCATGGCTG | CCGCCGCTTT | CGCCCTCGGG | GCGACTGTCT | TTGAGAGCGT | 950 |
| AGGCATGAGC | GATTATGCCG | TCACCCTCGA | ATCCGCTGCC | ATCGCCGCAT | 1000 |
| GGAATTGGAC | CATGGTCCAT | CCTCATGTGC | CTTTCGACAA | CACCGGATTT | 1050 |
| GCTTCCGTGA | GCCCCTCGCG | CAATGCCCAC | GATACGCTAG | CCAACCGTGT | 1100 |
| GATGGCCGCC | GCCATGCTCT | TCGAGCGCAC | GGGCGGTGCG | GTCTATCGCG | 1150 |
| ATTTCTTCGA | TGTGCGCTAT | CTCGATATGG | AGCCCGTGCA | GTGGTGGTAT | 1200 |
| TTCTTCCCCT | TTCAAGGTGA | GCTACAAAAA | GCTCTCGCCC | ACTACACGAC | 1250 |
| CCTCCCGGGA | GCGACGCCTA | GCGTCTCTGC | CGACATCCGC | AACCGGATGG | 1300 |
| CGGCTTCTAT | AAACGGTGGG | GAGTTTCTCG | GTGCATGGAA | TAACCAGACC | 1350 |
| GACGCCTACC | GCGCCTACCT | GAAGGATCAG | GATTACACGT | GGGGCTCGAA | 1400 |
| CAAAACAAAG | TCTCAGGCTG | GCTTTTTCTT | CGAGGGGGTA | CGGAGGCTTG | 1450 |
| GGCTCAACCC | CGCCGACGCG | GCCGCGCATC | GCGATGCCGC | GATGGGCTAC | 1500 |
| CTGCACTATC | TCCACGGAGT | GAACCCAATG | GGCATGGTCT | ATCTTAGCAA | 1550 |
| CATGTATGCC | AGCGGCGCTG | ACCGTGCAGC | CAATGAAATC | TACCACCATT | 1600 |
| GGTTCCGCGA | TGGCCGGACT | GGGACAATGC | CCTCACTTCA | CTCTACGGTC | 1650 |
| CCGCTCCTGG | TTTTCTTTCG | GGCGGGTCCC | AATGCCCAAA | TACAGCGGAA | 1700 |
| GCATTCAGGC | GATCCGAGAC | CAACCCGTGC | AAAAAGCCTA | CCTTGA | 1746 |

Figure 3
The translated 029cel protein composed of 581 amino acids

```
MNFSLPIRFF  GIGPTAGFFL  LLMGSSALVA  STHTDKIRID  QFGYPADATK   50
VAVIADPQIG  WNSAESYSPG  ATLEVRRVND  GVVVFSGSPV  PWNGGAIHIQ  100
SGDRVWWFDF  TVVAEPGHYR  IHDPANNTHS  DSFAIGADVY  DVVLREAVRM  150
FFYQRSGFAK  EVPYAHANWA  DAASHPQDVA  SRPIWDMGNA  SLERDLSGGW  200
FDAGDFNKYS  EWTGRVILEL  LLAYQGRPDV  FTDDFGIPES  GNGVPDLLDE  250
VKWGMDWLLR  MQEPSGAILG  KVSVTGHQSA  SPPSTDTHPR  YYGPVSTEAT  300
AMAAAAFALG  ATVFESVGMS  DYAVTLESAA  IAAWNWTMVH  PHVPFDNTGF  350
ASVSPSRNAH  DTLANRVMAA  AMLFERTGGA  VYRDFFDVRY  LDMEPVQWWY  400
FFPFQGELQK  ALAHYTTLPG  ATPSVSADIR  NRMAASINGG  EFLGAWNNQT  450
DAYRAYLKDQ  DYTWGSNKTK  SQAGFFFEGV  RRLGLNPADA  AAHRDAAMGY  500
LHYLHGVNPM  GMVYLSNMYA  SGADRAANEI  YHHWFRDGRT  GTMPSLHSTV  550
PLLVFFRAGP  NAQIQRKHSG  DPRPTRAKSL  P                       581
```

BACILLUS 029CEL CELLULASE

CROSS-REFERENCE TO RELATED APPLICATIONS

This application is a continuation (CON) of U.S. application Ser. No. 10/549,943 filed Aug. 21, 2006, now U.S. Pat. No. 7,604,974, which is a 371 of PCT/US04/13258 filed Apr. 28, 2004, which claim priority to U.S. Provisional Application No. 60/466,831 filed Apr. 29, 2003, which is herein incorporated in its entirety by reference.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to a novel cellulase referred to herein as 029cel. Also described are nucleic acids encoding the cellulase, compositions comprising said cellulase, methods of identifying novel cellulases and methods of using said compositions. Preferably the cellulase(s) are isolated from *Bacillus* species, preferably *B. agaradhaerens*. The present invention further relates to the use of the novel cellulase in compositions recognized in the art as advantageously having cellulase added thereto, including, as an additive in a detergent composition, in the treatment of cellulose containing fabrics, in the treatment of pulp and paper and in the treatment of starch for the production of high fructose corn-syrup or ethanol.

BACKGROUND OF THE INVENTION

Cellulose and hemicellulose are the most abundant plant materials produced by photosynthesis. They can be degraded and used as an energy source by numerous microorganisms, including bacteria, yeast and fungi, that produce extracellular enzymes capable of hydrolysis of the polymeric substrates to monomeric sugars (Aro et al., 2001). As the limits of non-renewable resources approach, the potential of cellulose to become a major renewable energy resource is enormous (Krishna et al., 2001). The effective utilization of cellulose through biological processes is one approach to overcoming the shortage of foods, feeds, and fuels (Ohmiya et al., 1997).

Cellulases are enzymes that hydrolyze cellulose (beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG"). (Knowles et al., 1987; Shulein, 1988). Endoglucanases act mainly on the amorphous parts of the cellulose fibre, whereas cellobiohydrolases are also able to degrade crystalline cellulose (Nevalainen and Penttila, 1995). Thus, the presence of a cellobiohydrolase in a cellulase system is required for efficient solubilization of crystalline cellulose (Suurnakki, et al. 2000). Beta-glucosidase acts to liberate D-glucose units from cellobiose, cello-oligosaccharides, and other glucosides (Freer, 1993).

In order to efficiently convert crystalline cellulose to glucose the complete cellulase system comprising components from each of the CBH, EG and BG classifications is required, with isolated components less effective in hydrolyzing crystalline cellulose (Filho et al., 1996). A synergistic relationship has been observed between cellulase components from different classifications. In particular, the EG-type cellulases and CBH-type cellulases synergistically interact to more efficiently degrade cellulose. See, e.g., Wood, 1985.

Although cellulase compositions have been previously described, there remains a need for new and improved cellulase compositions for use in household detergents, stone-washing compositions or laundry detergents, etc. Cellulases that exhibit improved performance are of particular interest.

BRIEF SUMMARY OF THE INVENTION

It is an object of the present invention to provide a novel cellulase having beneficial properties for use in detergents, treating textiles, biomass conversion and pulp and paper manufacturing.

It is an object of the present invention to provide polypeptides having cellulolytic activity and polynucleotides encoding the polypeptides. The polypeptides may improve the degradation of cell wall material, e.g., cellulose and/or hemicellulose. The polypeptides may also improve the stability or activity of other enzymes involved in the degradation of plant cell wall material, e.g., biomass.

An object of the present invention is to provide a novel cellulase and derivatives thereof, methods of producing such cellulases, and compositions comprising such novel cellulases. The present invention further relates to the use of the novel cellulase and derivatives thereof in compositions recognized in the art as advantageously having cellulase added thereto, including, as an additive in a detergent composition, in the treatment of textiles such as cellulose-containing fabrics and fibers useful therefor, as an animal feed additive, in biomass conversion, in the treatment of pulp and paper and in the treatment of starch for the production of high fructose corn-syrup or ethanol.

It is a further object of the present invention to provide for a method of producing a novel cellulase via heterologous expression from recombinant host cells.

It is yet a further object of the present invention to provide a nucleic acid sequence encoding the inventive cellulase. In one aspect, the nucleic acid and amino acid sequence facilitate commercial production of the novel cellulase and cellulase compositions of the invention.

It is still a further object of the present invention to provide a novel cellulase having excellent properties for use in detergents, treating textiles, as a feed supplement and in pulp and paper manufacturing. In a further aspect, the cellulase finds use in biomass conversion.

In a first aspect, the invention includes an isolated polynucleotide having a sequence which encodes 029cel, a sequence complementary to the 029cel gene coding sequence, and a composition comprising the polynucleotide. The polynucleotide may be mRNA, DNA, cDNA, genomic DNA, or an antisense analog thereof.

In one embodiment, a 029cel polynucleotide may comprise an isolated nucleic acid molecule which hybridizes to the complement of the nucleic acid presented as SEQ ID NO:2 under moderate to high stringency conditions, where the nucleic acid molecule encodes a 029cel polypeptide that exhibits cellulose binding activity.

The polynucleotide having at least 80%, 85%, 90%, 95%, 98% or more sequence identity to the sequence presented as SEQ ID NO:2 may encode a 029cel protein. In a specific embodiment, the polynucleotide comprises a sequence substantially identical to SEQ ID NO:2. The invention also contemplates fragments of the polynucleotide, preferably at least about 15-30 nucleotides in length.

In a second aspect, a novel cellulase or a derivative is provided which is obtainable from a *Bacillus*. Preferably, the cellulase of the invention comprises an amino acid sequence according to FIG. 3 (SEQ ID NO:3), a fragment, or a derivative thereof, having greater than 90% sequence identity, preferably greater than 95% sequence identity and more preferably greater than 97% sequence identity to an active portion thereto.

In a third aspect the present invention relates to a nucleic acid construct comprising the nucleotide sequence, which encodes for the polypeptide of the invention, operably linked to one or more control sequences that direct the production of the polypeptide in a suitable host.

The invention further provides recombinant expression vectors containing a nucleic acid sequence encoding 029cel or a fragment or splice variant thereof, operably linked to regulatory elements effective for expression of the protein in a selected host. In a related aspect, the invention includes a host cell containing the vector.

In a fourth aspect the present invention relates to a recombinant expression vector comprising the nucleic acid construct of the invention.

In a fifth aspect the present invention relates to a recombinant host cell comprising the nucleic acid construct of the invention.

The invention further includes a method for producing 029cel by recombinant techniques, by culturing recombinant prokaryotic or eukaryotic host cells comprising nucleic acid sequence encoding 029cel under conditions effective to promote expression of the protein, and subsequent recovery of the protein from the host cell or the cell culture medium.

In a sixth aspect the present invention relates to a method for producing a polypeptide of the invention, the method comprising: (a) cultivating a microorganism, which in its wild-type form is capable of producing the polypeptide, to produce the polypeptide; and (b) recovering the polypeptide.

In a seventh aspect the invention provides for an enzymatic composition useful in the conversion of cellulose to ethanol. In a preferred embodiment the enzymatic composition comprises 029cel. The composition may further comprise additional cellulase enzymes such as endoglucanases and/or cellobiohydrolases. The composition may be enriched in 029cel.

In one embodiment the invention provides a method of identifying novel enzymes by isolating total microbial community DNA from an environment, constructing a genomic DNA library in *E. coli*, screening the library for expression of cellulase activity, identifying the cellulase gene in the cellulase-positive clone and characterising the novel cellulase enzyme.

Further provided herein are analytical methods for detecting 029cel nucleic acids and 029cel proteins also form part of the invention.

According to yet another embodiment of the invention, a method of transforming a suitable microorganism with nucleic acid sequence encoding a cellulase according to the invention is provided. A method of producing the cellulase according to the invention from said transformed microorganism is provided.

A further object of the invention is to provide an expression vector particularly effective in *Streptomyces*. *Streptomyces* serve as alternate host cells for the production of various proteins and with respect to the expression and production of cellulases may offer a number of advantages over *Bacillus* host cells particularly when cells are grown at a high cell density. A preferred expression vector comprises a regulatory polynucleotide sequence including a promoter sequence derived from a glucose isomerase gene of *Actinoplanes*, a signal sequence derived from a *Streptomyces* cellulase gene, and a DNA sequence encoding a cellulase, particularly a cellulase according to the invention.

In a preferred embodiment of the present invention, a full-length cellulase is obtainable from *Bacillus*.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 1 illustrates the environmental nucleotide sequence (SEQ ID NO:1).

FIG. 2 illustrates a nucleic acid sequence encoding the novel cellulase (SEQ ID NO:2).

FIG. 3 illustrates the deduced amino acid sequence of the inventive cellulase (SEQ ID NO:3).

DETAILED DESCRIPTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. Definitions

"Cellulase," "cellulolytic enzymes" or "cellulase enzymes" means the inventive bacterial endoglucanase described herein. Three different types of cellulase enzymes act synergistically to convert cellulose and its derivatives to glucose.

The term "cellulase" refers to a category of enzymes capable of hydrolyzing cellulose polymers to shorter cello-oligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, and bacteria. The enzymes made by these microbes are mixtures of proteins with three types of actions useful in the conversion of cellulose to glucose: endoglucanases (EG), cellobiohydrolases (CBH), and beta-glucosidase. These three different types of cellulase enzymes act synergistically to convert cellulose and its derivatives to glucose.

Many microbes make enzymes that hydrolyze cellulose, including the wood rotting fungus *Trichoderma*, the compost bacteria *Thermomonospora, Bacillus*, and *Cellulomonas; Streptomyces*; and the fungi *Humicola, Aspergillus* and *Fusarium*.

By the term "host cell" is meant a cell that contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. In a one embodiment according to the present invention, "host cell" means the cells of the genus *Bacillus*. In another preferred embodiment according to the invention, "host cell" means the cells of *Streptomyces*. A *Streptomyces* means any bacterial strain that is a member of the genus *Streptomyces* as classified in Buchanan et al., *The Shorter Bergey's Manual For Determinative Bacteriology* (Williams & Wilkens 1982). Particularly preferred strains of *Streptomyces* include *S. lividens, S. rubiginosus*, and *S. coelicolor. S. lividens* is described in Lomovskaya et al., *J. Virology* 9:258 (1972). However, one of skill will realize that any appropriate host cell, e.g., bacterial, fungal, eukaryotic and plant cell may be used.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "secretory signal sequence" denotes a DNA sequence that encodes a polypeptide (a "secretory peptide" or "secretory signal peptide") that, as a component of a larger polypeptide, directs the larger polypeptide through a secretory pathway of a cell in which it is synthesized. The larger peptide is commonly cleaved to remove the secretory peptide during transit through the secretory pathway to yield the secretory signal peptide and a smaller peptide commonly referred to as the mature polypeptide.

As used herein, the phrases "whole cellulase preparation" and "whole cellulase composition" are used interchangeably and refer to both naturally occurring and non-naturally occurring compositions. A "naturally occurring" composition is one produced by a naturally occurring source and which comprises, for example, one or more cellobiohydrolase-type, one or more endoglucanase-type, and one or more β3-glucosidase components wherein each of these components is found at the ratio produced by the source. Certain fungi produce complete cellulase systems which include exo-cellobiohydrolases or CBH-type cellulases, endoglucanases or EG-type cellulases and beta-glucosidases or BG-type cellulases (Schulein, 1988). However, sometimes these systems lack CBH-type cellulases and bacterial cellulases also typically include little or no CBH-type cellulases. A naturally occurring composition is one that is produced by an organism unmodified with respect to the cellulolytic enzymes such that the ratio of the component enzymes is unaltered from that produced by the native organism.

A "non-naturally occurring" composition encompasses those compositions produced by: (1) combining component cellulolytic enzymes either in a naturally occurring ratio or non-naturally occurring, i.e., altered, ratio; or (2) modifying an organism to overexpress or underexpress one or more cellulolytic enzyme; or (3) modifying an organism such that at least one cellulolytic enzyme is deleted or (4) modifying an organism to express a heterologous component cellulolytic enzyme.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. The promoter may be the promoter normally associated with the downstream gene or it may be heterologous, i.e., from another gene or another microorganism as long as it function to direct the gene. A preferred promoter when the transformation host cell is *Bacillus* is the apre promoter. In one aspect the promoter is an inducible promoter. In one aspect, when the host cell is a filamentous fungus, the promoter is the *T. reesei* cbh1 promoter which is deposited in GenBank under Accession Number D86235. In another aspect the promoter is a cbh II or xylanase promoter from *T. reesei*.

A nucleic acid is "operably linked" when it is placed into a functional relationship with another nucleic acid sequence. For example, DNA encoding a secretory leader, i.e., a signal peptide, is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"DNA construct" or "DNA vector" means a nucleotide sequence which comprises one or more DNA fragments encoding the novel cellulase. Included in "DNA vectors" are "expression vectors." Typical expression vectors contain regulatory sequences such as, transcription and translation terminators, transcription and translation initiation sequences, signal sequences, and promoters useful for regulation of the expression of the particular nucleic acid. The term "promoter" is used in its ordinary sense to refer to a polynucleotide sequence involved in the control of the initiation of transcription of a polynucleotide sequence encoding a protein. A "signal sequence" refers to a signal peptide or a portion of a protein that is capable of directing the transport of a desired protein in bioactive form from a host. The mature form of an extracellular protein lacks the signal sequence which is cleaved off during the secretion process. While not meant to limit the invention, the number of amino acid residues in a signal peptide may be between about 5 and about 100 amino acid residues. Signal sequence may be modified to provide for cloning sites that allow for the ligation of DNA or insertion of DNA encoding a cellulase. The vectors optionally comprise generic expression cassettes containing at least one independent terminator sequence, sequences permitting replication of the cassette in prokaryotes, eukaryotes, or both, (e.g., shuttle vectors) and selection markers for both prokaryotic and eukaryotic systems. Vectors are suitable for replication and integration in prokaryotes, eukaryotes, or both. See, Giliman and Smith, *Gene* 8:81-97 (1979); Roberts et al., *Nature* 328:731-734 (1987); Berger and Kimmel, GUIDE TO MOLECULAR CLONING TECHNIQUES, METHODS IN ENZYMOLOGY, VOL 152, Academic Press, Inc., San Diego, Calif. ("Berger"); Scheider, B., et al., *Protein Expr. Purif* 6435:10 (1995); Sambrook et al. MOLECULAR CLONING—A LABORATORY MANUAL (2ND ED.) VOL. 1-3, Cold Springs Harbor Publishing (1989) ("Sambrook"); and CURRENT PROTOCOLS 1N MOLECULAR BIOLOGY, Ausubel et al. (eds.), Current Protocols, a joint venture between Greene Publishing Associates, Inc. and John Wiley & Sons, Inc., (1997 Supplement) ("Ausubel"). Cloning vectors useful in *Streptomyces* are known and reference is made to U.S. Pat. Nos. 4,338,397; 4,411,994; 4,513,085; 4,513,086; 4,745,056; 5,514,590; and 5,622,866 and WO88/07079.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

The term "% homology" is used interchangeably herein with the term "% identity" herein and refers to the level of nucleic acid or amino acid sequence identity between the nucleic acid sequence that encodes 029cel or the 029cel amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for 029cel, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at www.ncbi.nlm.nih.gov/BLAST. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

The terms "isolated" or "purified" as used herein refer to a nucleic acid or amino acid that is removed from at least one component with which it is naturally associated.

In the present context, the term "substantially pure polypeptide" means a polypeptide preparation which contains at the most 10% by weight of other polypeptide material with which it is natively associated (lower percentages of other polypeptide material are preferred, e.g. at the most 8% by weight, at the most 6% by weight, at the most 5% by weight, at the most 4% at the most 3% by weight, at the most 2% by weight, at the most 1% by weight, and at the most ½% by weight). Thus, it is preferred that the substantially pure polypeptide is at least 92% pure, i.e. that the polypeptide constitutes at least 92% by weight of the total polypeptide material present in the preparation, and higher percentages are preferred such as at least 94% pure, at least 95% pure, at least 96% pure, at least 96% pure, at least 97% pure, at least 98% pure, at least 99%, and at the most 99.5% pure. The polypeptides disclosed herein are preferably in a substantially pure form. In particular, it is preferred that the polypeptides disclosed herein are in "essentially pure form", i.e. that the polypeptide preparation is essentially free of other polypeptide material with which it is natively associated. This can be accomplished, for example, by preparing the polypeptide by means of well-known recombinant methods. Herein, the term "substantially pure polypeptide" is synonymous with the terms "isolated polypeptide" and "polypeptide in isolated form".

In general, nucleic acid molecules which encode the 029cel will hybridize, under moderate to high stringency conditions to the sequence provided herein as SEQ ID NO:2 (the 029cel). However, in some cases a 029cel-encoding nucleotide sequence is employed that possesses a substantially different codon usage, while the protein encoded by the 029cel-encoding nucleotide sequence has the same or substantially the same amino acid sequence as the native protein. For example, the coding sequence may be modified to facilitate faster expression of 029cel in a particular prokaryotic or eukaryotic expression system, in accordance with the frequency with which a particular codon is utilized by the host. Te'o, et al. (2000), for example, describes the optimization of genes for expression in filamentous fungi.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm−5° C. (5° below the Tm of the probe); "high stringency" at about 5-10° below the Tm; "moderate" or "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "029cel expression" refers to transcription and translation of the 029cel cellulase gene, the products of which include precursor RNA, mRNA, polypeptide, post-translationally processed polypeptides. By way of example, assays for 029cel expression include Western blot for 029cel protein, Northern blot analysis and reverse transcriptase polymerase chain reaction (RT-PCR) assays for 029cel mRNA, and endoglucanase activity assays as described in Shoemaker S. P. and Brown R. D. Jr. (Biochim. Biophys. Acta, 1978, 523:133-146) and Schulein (1988).

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

As used herein, the term "detergent composition" refers to a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the terms "active" and "biologically active" refer to a biological activity associated with a particular protein and are used interchangeably herein. For example, the enzymatic activity associated with a protease is proteolysis and, thus, an active protease has proteolytic activity. It follows that the biological activity of a given protein refers to any biological activity typically attributed to that protein by those of skill in the art.

When employed in enzymatic solutions, the 029cel component is generally added in an amount sufficient to allow the highest rate of release of soluble sugars from the biomass. The amount of 029cel component added depends upon the type of biomass to be saccharified which can be readily determined by the skilled artisan. However, when employed, the weight percent of the 029cel component relative to any other cellulase type components present in the cellulase composition is from preferably about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 30 weight percent, from about 15 to about 45 weight percent, from about 15 to about 50 weight percent.

II. Molecular Biology

This invention relies on routine techniques in the field of recombinant genetics. Basic texts disclosing the general methods of use in this invention include Sambrook et al., *Molecular Cloning, A Laboratory Manual* (2nd ed. 1989);

Kriegler, *Gene Transfer and Expression: A Laboratory Manual* (1990); and Ausubel et al., eds., *Current Protocols in Molecular Biology* (1994)).

To obtain high level expression of a cloned gene, the heterologous gene is preferably positioned about the same distance from the promoter as is in the naturally occurring cellulase gene. As is known in the art, however, some variation in this distance can be accommodated without loss of promoter function.

Those skilled in the art are aware that a natural promoter can be modified by replacement, substitution, addition or elimination of one or more nucleotides without changing its function. The practice of the invention encompasses and is not constrained by such alterations to the promoter.

The expression vector/construct typically contains a transcription unit or expression cassette that contains all the additional elements required for the expression of the heterologous sequence. A typical expression cassette thus contains a promoter operably linked to the heterologous nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

The practice of the invention is not constrained by the choice of promoter in the genetic construct. The only constraint on the choice of promoter is that it is functional in the host cell used. A preferred promoter when the transformation host cell is *Bacillus* is the aprE promoter.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include bacteriophages λ and M13, as well as plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

The elements that are typically included in expression vectors also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable.

The methods of transformation of the present invention may result in the stable integration of all or part of the transformation vector into the genome of the filamentous fungus. However, transformation resulting in the maintenance of a self-replicating extra-chromosomal transformation vector is also contemplated.

The gene encoding the cellulase of the present invention can be cloned using λ-phage (expression) vectors and *E. coli* host cells. (Alternatively PCR cloning using consensus primers designed on conserved domains may be used.) Applicants have discovered that transformation of the gene encoding the cellulase of the present invention and expression in *E. coli* results in an active protein. After a first cloning step in *E. coli*, a cellulase gene according to the present invention can be transferred to a more preferred industrial expression host such as *Bacillus* or *Streptomyces* species, a filamentous fungus such as *Aspergillus* or *Trichoderma*, or a yeast such as *Saccharomyces*. High level expression and secretion obtainable in these host organisms allows accumulation of the cellulase in the fermentation medium from which it can subsequently be recovered.

A preferred general transformation and expression protocol for protease deleted *Bacillus* strains is provided in Ferrari et al., U.S. Pat. No. 5,264,366, incorporated herein by reference. Transformation and expression in *Aspergillus* is described in, for example, Berka et al., U.S. Pat. No. 5,364,770, incorporated herein by reference.

Many, standard transfection methods can be used to produce *Trichoderma reesei* cell lines that express large quantities of the heterologus protein. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138), all incorporated herein by reference.

However, any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the heterologous gene.

After the expression vector is introduced into the cells, the transfected cells are cultured under conditions favoring expression of genes under control of cellulase gene promoter sequences. Large batches of transformed cells can be cultured as described below. Finally, product is recovered from the culture using standard techniques.

Thus, the invention herein provides for the expression and enhanced secretion of the inventive cellulases whose expression is under control of cellulase gene promoter sequences including naturally occurring cellulase genes, fusion DNA sequences, and various heterologous constructs. The invention also provides processes for expressing and secreting high levels of the inventive cellulases.

III. Identification of Nucleic Acids and Encoded Protein Sequences

A genomic library from *Bacillus agaradhaerans* (DSM 8721) was prepared using standard techniques known in the art. This organism produces an alkaline cellulase, (endo-1,4-beta-glucanase), belonging to cellulase family 5 of glycosyl hydrolases, endoglucanase 5A, EC 3.2.1.4, Swiss-Prot: O85465, entry name GUN5_BACAG. EBI accession number AF067428) the gene for which is 1203 bp in length, (Davies et al. 1998). Cellulase positive clones were detected with an incidence of $1/3000$ in the plate assay. In the process for isolating a gene according to an aspect of the present invention, degenerate primers based on the coding sequence for this enzyme were used. Unexpectedly, however, no PCR product was obtained using primers known to amplify the known *B. agaradhaerans* cellulase. The complete sequence of the insert coding for the cellulase was therefore determined by primer walking.

The process for isolating a gene according to the second aspect of the present invention makes use of its homology to a nucleotide sequence comprising all or part of the nucleotide sequence of SEQ ID No.:1 or SEQ ID No:2 as shown in the sequence listing. Examples of such processes include:
  a) screening a gene library which presumably contains a 029cel gene using the nucleotide sequence as a probe.
  b) preparing a primer based on the nucleotide sequence information, then performing PCR using a sample which presumably contains a 029cel gene as a template.

More specifically, process a) above comprises:
  a) preparing a gene library which presumably contains a cellulase gene, screening the gene library using a nucleotide sequence comprising all or part of the nucleotide sequence of SEQ ID No:2 as shown in the sequence listing to select sequences which hybridize with the nucleotide sequence comprising all or part of the nucleotide sequence of SEQ ID No:2 as shown in the sequence listing from the gene library, then isolating the selected sequences, and isolating a 029cel gene from the sequences which have been selected and isolated from the gene library.

The gene library may be a genomic DNA library or a cDNA library, and may be prepared according to a known procedure.

IV. Protein Expression

Proteins of the present invention are produced by culturing cells transformed with an expression vector containing the inventive cellulase gene whose expression is under control of promoter sequences. The present invention is particularly useful for enhancing the intracellular and/or extracellular production of proteins. The protein may be homologous or heterologous.

Proteins of the present invention may also be modified in a way to form chimeric molecules comprising a protein of interest fused to another, heterologous polypeptide or amino acid sequence. In one embodiment, such a chimeric molecule comprises a fusion of the protein of interest with a tag polypeptide which provides an epitope to which an anti-tag antibody can selectively bind. The epitope tag is generally placed at the amino- or carboxyl-terminus of the protein of interest.

Various tag polypeptides and their respective antibodies are well known in the art. Examples include poly-histdine (poly-his) or poly-histidine-glycine (poly-his-gly) tags; HIS6 and metal chelation tags, the flu HA tag polypeptide and its antibody 12CA5 (Field et al., *Mol. Cell. Biol.* 8:2159-2165 (1988)); the c-myc tag and the 8F9, 3C7, 6E10, G4, B7 and 9E10 antibodies thereto (Evan et al., *Molecular and Cellular Biology* 5:3610-3616 (1985)); and the Herpes Simplex virus glycoprotein D (gD) tag and its antibody (Paborsky et al., Protein Engineering 3(6):547-553 (1990)). Other tag polypeptides include the FLAG-peptide (Hopp et al., *BioTechnology* 6:1204-1210 (1988)); the KT3 epitope peptide (Martin et al., *Science* 255:192-194 (1992)); tubulin epitope peptide (Skinner et al., *J. Biol. Chem.* 266:15163-15166 (1991)); and the T7 gene 10 protein peptide tag (Lutz-Freyermuth et al., *Proc. Natl. Acad. Sci. USA* 87:6393-6397 (1990)).

Conditions appropriate for expression of said 029cel gene comprises providing to the culture the components necessary for growth and/or expression of the inventive cellulase. Optimal conditions for the production of the proteins will vary with the choice of the host cell, and with the choice of protein to be expressed. Such conditions will be easily ascertained by one skilled in the art through routine experimentation or optimization.

The protein of interest is typically purified or isolated after expression. The protein of interest may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the protein of interest may be purified using a standard anti-protein of interest antibody column. Ultrafiltration and diafiltration techniques, in conjunction with protein concentration, are also useful. For general guidance in suitable purification techniques, see Scopes, Protein Purification (1982). The degree of purification necessary will vary depending on the use of the protein of interest. In some instances no purification will be necessary.

V. Utility of Cellulase

Treatment of textiles according to the present invention contemplates textile processing or cleaning with a composition comprising the cellulase of this invention. Such treating includes, but is not limited to, stonewashing, modifying the texture, feel and/or appearance of cellulose-containing fabrics or other techniques used during manufacturing or cleaning/reconditioning of cellulose-containing fabrics. Additionally, treating within the context of this invention contemplates the removal of "immature" or "dead" cotton from cellulosic fabric or fibers. Immature cotton is significantly more amorphous than mature cotton and because of, for example, uneven dyeing. The composition contemplated in the present invention further includes a cellulase component for use in washing a soiled manufactured cellulose-containing fabric. For example, a cellulase of this invention may be used in a detergent composition for washing laundry. Detergent compositions useful in accordance with the present invention include special formulations such as pre-wash, pre-soak and home-use color restoration compositions. Such treating compositions, as described herein, may be in the form of a concentrate which requires dilution or in the form of a dilute solution or a form which can be applied directly to the cellulose-containing fabric. General treatment techniques for cellulase treatment of textiles are described in, for example, EP Publication No. 220 016 and GB Application Nos. 1,368,599 and 2,095,275.

Treatment of a cellulosic material according to the present invention further contemplates the treatment of animal feed, pulp and/or paper, food and grain for purposes known in the art. For example, cellulases are known to increase the value of animal feed, improve the drainability of wood pulp, enhance food products and reduce fiber in grain during the grain wet milling process or dry milling process.

Treating according to the instant invention comprises preparing an aqueous solution which contains an effective amount of a cellulase or a combination of cellulases together with other optional ingredients including, for example, a buffer, a surfactant, and/or a scouring agent. An effective amount of a cellulase enzyme composition is a concentration of cellulase enzyme sufficient for its intended purpose. Thus, for example, an "effective amount" of cellulase in a stonewashing composition according to the present invention is that amount which will provide the desired effect, e.g., to produce a worn and faded look in seams and on fabric panels. Similarly, an "effective amount" of cellulase in a composition intended for improving the feel and/or appearance of a cellulose-containing fabric is the amount that produces measurable improvements in the feel, e.g., improving the smoothness of the fabric, or appearance, e.g., removing pills and fibrils which tend to reduce the sharpness in appearance of a fabric. The amount of cellulase employed is also dependent on the equipment employed, the process parameters employed (the temperature of the cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric to be treated is added can be readily determined by the skilled artisan based on the above factors as well as the desired result. In stonewashing processes, it has generally been preferred that the cellulase be present in the aqueous treating solution in a concentration of from about 0.5 to 5,000 ppm and most preferably about 10 to 200 ppm total protein. In compositions for the improvement of feel and/or appearance of a cellulose-containing fabric, it has generally been preferred that the cellulase be present in the aqueous treating solution in a concentration of from about 0.1 to 2000 ppm and most preferably about 0.5 to 200 ppm total protein.

In a preferred treating embodiment, a buffer is employed in the treating composition such that the concentration of buffer is sufficient to maintain the pH of the solution within the range wherein the employed cellulase exhibits activity. The pH at which the cellulase exhibits activity depends on the nature of the cellulase employed. The exact concentration of buffer employed will depend on several factors which the skilled artisan can readily take into account. For example, in a preferred embodiment, the buffer as well as the buffer concentration are selected so as to maintain the pH of the final cellulase solution within the pH range required for optimal cellulase activity. The determination of the optimal pH range of the cellulases of the invention can be ascertained according to well-known techniques. Suitable buffers at pH within the activity range of the cellulase are also well known to those skilled in the art in the field.

In addition to cellulase and a buffer, the treating composition may optionally contain a surfactant. Suitable surfactants include any surfactant compatible with the cellulase being utilized and the fabric including, for example, anionic, non-ionic and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include, but are not limited to, alkali metal ions such as sodium and potassium; alkaline earth metal ions such as calcium and magnesium; ammonium ion; and alkanolamines having 1 to 3 alkanol groups of carbon number 2 or 3. Ampholytic surfactants include, e.g., quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

A concentrated cellulase composition can be prepared for use in the methods described herein. Such concentrates contain concentrated amounts of the cellulase composition described above, buffer and surfactant, preferably in an aqueous solution. When so formulated, the cellulase concentrate can readily be diluted with water so as to quickly and accurately prepare cellulase preparations having the requisite concentration of each constituent. When aqueous concentrates are formulated, these concentrates can be diluted so as to arrive at the requisite concentration of the components in the cellulase solution as indicated above. As is readily apparent, such cellulase concentrates permit facile formulation of the cellulase solutions as well as permit feasible transportation of the composition to the location where it will be used. The treating concentrate can be in any art-recognized form, for example, liquid, emulsion, gel, or paste. Such forms are well known to those skilled in the art.

When a solid cellulase concentrate is employed, the cellulase composition may be a granule, a powder, an agglomerate or a solid disk. The granules can be formulated so as to contain materials to reduce the rate of dissolution of the granules into the wash medium. Such materials and granules are disclosed in U.S. Pat. No. 5,254,283 which is incorporated herein by reference in its entirety.

Other materials can also be used with or placed in the cellulase composition of the present invention as desired, including stones, pumice, fillers, solvents, enzyme activators, and anti-redeposition agents depending on the eventual use of the composition.

By way of example, stonewashing methods will be described in detail, however, the parameters described are readily modified by the skilled artisan for other applications, i.e., improving the feel and/or appearance of a fabric. The cellulose-containing fabric is contacted with the cellulase containing stonewashing composition containing an effective amount of the cellulase by intermingling the treating composition with the stonewashing composition, and thus bringing the cellulase enzyme into proximity with the fabric. Subsequently, the aqueous solution containing the cellulase and the fabric is agitated. If the treating composition is an aqueous solution, the fabric may be directly soaked in the solution. Similarly, where the stonewashing composition is a concentrate, the concentrate is diluted into a water bath with the cellulose-containing fabric. When the stonewashing composition is in a solid form, for example a pre-wash gel or solid stick, the stonewashing composition may be contacted by directly applying the composition to the fabric or to the wash liquor.

The cellulose-containing fabric is incubated with the stonewashing solution under conditions effective to allow the enzymatic action to confer a stonewashed appearance to the cellulose-containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature which allow the cellulase enzyme to react efficiently with cellulose-containing fabric, in this case to produce the stonewashed effect. It is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from about 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature, which temperature is dependent on the nature of the cellulase used. Thus, if the reaction temperature is permitted to go too high, the cellulolytic activity is lost as a result of the denaturing of the cellulase. While standard temperatures for cellulase usage in the art are generally in the range of 35° C. to 65° C., and these conditions would also be expected to be suitable for the cellulase of the invention, the optimal temperature conditions should be ascertained according to well known techniques with respect to the specific cellulase used.

Reaction times are dependent on the specific conditions under which the stonewashing occurs. For example, pH, temperature and concentration of cellulase will all affect the optimal reaction time. Generally, reaction times are from about 5 minutes to about 5 hours, and preferably from about 10 minutes to about 3 hours and, more preferably, from about 20 minutes to about 1 hour.

According to yet another preferred embodiment of the present invention, the cellulase of the invention may be employed in a detergent composition. The detergent compositions according to the present invention are useful as pre-wash compositions, pre-soak compositions, or for cleaning during the regular wash or rinse cycle. Preferably, the detergent composition of the present invention comprises an effective amount of cellulase, a surfactant, and optionally includes other ingredients described below.

An effective amount of cellulase employed in the detergent compositions of this invention is an amount sufficient to impart the desirable effects known to be produced by cellulase on cellulose-containing fabrics, for example, depilling, softening, anti-pilling, surface fiber removal, anti-graying and cleaning. Preferably, the cellulase in the detergent composition is employed in a concentration of from about 10 ppm to about 20,000 ppm of detergent.

The concentration of cellulase enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The amount of cellulase enzyme employled in the detergent composition will depend on the extent to which the detergent will be diluted upon addition to water so as to form a wash solution.

The detergent compositions of the present invention may be in any art recognized form, for example, as a liquid, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase protecting agent. The granule can be formulated so as to contain materials to reduce the rate of dissolution of the granule into the wash medium. Such materials and granules are disclosed in U.S. Pat. No. 5,254,283 which is incorporated herein by reference in its entirety.

The detergent compositions of this invention employ a surface active agent, i.e., surfactant, including anionic, non-ionic and ampholytic surfactants well known for their use in detergent compositions.

Suitable anionic surfactants for use in the detergent composition of this invention include linear or branched alkylbenzenesulfonates; alkyl or alkenyl ether sulfates having linear or branched alkyl groups or alkenyl groups; alkyl or alkenyl sulfates; olefinsulfonates; and alkanesul-fonates. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyal-kylene ethers, as well as higher fatty acid alkanolamides or alkylene oxide adduct thereof, fatty acid glycerine monoesters, and the like. Suitable surfactants for use in this invention are disclosed in British Patent Application No. 2 094 826 A, the disclosure of which is incorporated herein by reference. Mixtures of such surfactants can also be used. The surfactant or a mixture of surfactants is generally employed in the detergent compositions of this invention in an amount from about 1 weight percent to about 95 weight percent of the total detergent composition and preferably from about 5 weight percent to about 45 weight percent of the total detergent composition. In addition to the cellulase composition and the surfactant(s), the detergent compositions of this invention can optionally contain one or more of the following components:

Hydrolases Except Cellulase

Suitable hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and a-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) α-amylase, β-amylase, gluco amylase, invertase, lysozyme, pectinase, chitinase, and dextranase. Preferably among them are α-amylase and β-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified protein. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Cationic Surfactants and Long-Chain Fatty Acid Salts

Such cationic surfactants and long-chain fatty acid salts include saturated or unsaturated fatty acid salts, alkyl or alkenyl ether carboxylic acid salts, α-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

Builders

A. Divalent Sequestering Agents

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering gents are disclosed in British Patent Application No. 2 094 826 A, the disclosure of which is incorporated herein by reference.

B. Alkalis or Inorganic Electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition Agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose and/or polyethylene glycol with the cellulase composition of the present invention provides for an especially useful dirt removing composition.

Bleaching Agents

The use of the cellulase of the present invention in combination with a bleaching agent such as potassium monopersulfate, sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the detergenting effects. Similarly, bleaching agents and bleach catalysts as described in EP 684 304 may be used.

Bluing Agents and Fluorescent Dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking Inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, amorphous silicas, clay, calcium silicate (such as Micro-Cell of Johns Manville Co.), calcium carbonate and magnesium oxide.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1-bis(4 hydroxy-phenyl)cyclohexane.

Solubilizers

The solubilizers include, for example, lower alcohols such as ethanol, benzenesulfonate salts, lower alkylbenzenesulfonate salts such as p-toluenesulfonate salts, glycols such as propylene glycol, acetylbenzene-sulfonate salts, acetamides, pyridinedicarboxylic acid amides, benzoate salts and urea.

The detergent composition of the present invention can be used in a broad pH range from acidic to alkaline pH. In a preferred embodiment, the detergent composition of the present invention can be used in mildly acidic, neutral or alkaline detergent wash media having a pH of from above 5 to no more than about 12.

Aside from the above ingredients, perfumes, buffers, preservatives, dyes and the like can be used, if desired, with the detergent compositions of this invention. Such components are conventionally employed in amounts heretofore used in the art.

When a detergent base used in the present invention is in the form of a powder, it may be one which is prepared by any known preparation methods including a spray-drying method and a granulation method. The detergent base obtained particularly by the spray-drying method, agglomeration method, dry mixing method or non-tower route methods are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. After the spray-drying, perfumes, enzymes, bleaching agents, inorganic alkaline builders may be added. With a highly dense, granular detergent base obtained such as by the spray-drying-granulation or agglomeration method, various ingredients may also be added after the preparation of the base.

When the detergent base is a liquid, it may be either a homogeneous solution or a nonhomogeneous dispersion. For removing the decomposition of carboxymethylcellulose by the cellulase in the detergent, it is desirable that carboxymethylcellulose is granulated or coated before the incorporation in the composition.

The detergent compositions of this invention may be incubated with cellulose-containing fabric, for example soiled fabrics, in industrial and household uses at temperatures, reaction times and liquor ratios conventionally employed in these environments.

Detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the cellulase enzyme is generally employed from about 0.0001 to about 1 weight percent based on the total weight of the pre-soak or pre-treatment composition. In such compositions, a surfactant may optionally be employed and when employed, is generally present at a concentration of from about 0.005 to about 20 weight percent based on the total weight of the pre-soak. The remainder of the composition comprises conventional components used in the pre-soak, i.e., diluent, buffers, other enzymes (proteases), and the like at their conventional concentrations.

It is contemplated that compositions comprising cellulase enzymes described herein can be used in home use as a stand alone composition suitable for restoring color to faded fabrics (see, for example, U.S. Pat. No. 4,738,682, which is incorporated herein by reference in its entirety) as well as used in a spot-remover and for depilling and antipilling (pilling prevention).

The use of the cellulase according to the invention may be particularly effective in feed additives and in the processing of pulp and paper. These additional industrial applications are described in, for example, PCT Publication No. 95/16360 and Finnish Granted Patent No. 87372, respectively.

In order to further illustrate the present invention and advantages thereof, the following specific examples are given with the understanding that they are being offered to illustrate the present invention and should not be construed in any way as limiting its scope.

EXAMPLES

The following examples are offered to illustrate, but not to limit the claimed invention.

Example 1

Sample Collection and Processing

This example illustrates how to collect samples and process them to obtain sufficient DNA to create a cDNA library.

Samples of water (250 ml) were collected from the littoral zone of Sonachi (Crater) Lake, Kenya using a 250-ml stainless steel beaker mounted on the end of a flexible extendible 1-m pole and placed in sealable plastic containers (Whiripak) for transport to the laboratory at ambient temperature. The temperature of the surface waters was 28° C., with pH 10 and a conductivity of 7.23 mS cm$^{-1}$ (at 27° C.).

To collect the microbial flora, water (750 ml) from Sonachi (Crater) Lake, Kenya was filtered on site (using a hand operated vacuum pump) through a sequence of sterile membrane filters (47 mm diameter), composed of cellulose nitrate or cellulose acetate, of decreasing pore size, until all water flow stopped. The sequence of filters was 8.1 1m, 3 μm and 0.22 μm. The individual membrane filters were placed immediately into 10 ml of cold, sterile cell stabilization buffer (TES) containing 10 mM Tris HCl, pH 8.0; 1 mM EDTA and 5% w/v NaCl in 30 ml sterile plastic universal tubes and kept on ice in a refrigerated cool box until they could be processed further, usually within 4 hours of sampling. The microbial material on the filters was dispersed by vigorous vortex mixing with sterile glass beads (5 ml) and the cells pelleted in microfuge tubes by centrifugation at 13,000 g for 5 min. The microbial material was aliquoted to the microfuge tubes in volumes estimated to contain the equivalent of $10^8$ to $10^9$ bacterial cells, giving a total of 12 tubes. The DNA was extracted using the GenomicPrep™ Cells and Tissue DNA isolation kit (Amersham Pharmacia Biotech, Piscataway, N.J., USA) following the manufacturer's instructions. Cells in each tube were resuspended in 600 μl of the Cell Lysis Solution provided, and incubated at 80° C. for 5 min to lyse the cells. Samples prepared by this method are stable at room temperature for at least 18 months, and were transported back to the laboratory in this form. DNA extraction was completed by RNase A treatment, protein precipitation and isopropanol precipitation of the DNA following the manufacturer's protocol. Each DNA pellet was dissolved in 100 μl sterile Tris buffer 10 mM pH 8.5.

DNA yield was estimated by running 5 μl samples on a 0.5% w/v agarose gel and comparing with known amounts of bacterial genomic DNA. The samples were pooled, giving a total of about 20 μg DNA. Since yields were low, the material was supplemented with about 30% extra material extracted from the water samples which were collected at the same time as the on-site material and stored at 4° C. in the laboratory until required. This amount of DNA, about 30 μg, was the amount of starting material that preliminary experiments had shown was needed to carry out the trial and bulk restriction digestion and size fractionation to give sufficient material for library construction.

Example 2

Library Construction

The following example details how to prepare a DNA library for use in screening and detection of novel sequences in E. coli.

Preparation of DNA

The pooled DNA was used for construction of the genomic DNA library. The purified DNA was partially digested with Sau3A1 to give an average fragment size of about 5 kb. Restricted DNA was size fractionated by electrophoresis on 0.5% agarose in TAE (0.04M Tris-acetate, 0.001M EDTA pH 8.0). Material in the 1.5 to 10 kb range was excised and replaced in a well of the same size cut in an unused part of the agarose gel and concentrated to a narrow band by reversed electrical current. The DNA band was excised and DNA extracted using the QIAGEN (Crawley, UK) QIAEXII gel extraction kit, following the manufacturer's guidelines. The eluted DNA was precipitated with ethanol and resuspended in 10 mM Tris HCl buffer, pH 8.5.

Preparation of Lambda Libraries

The restricted DNA was cloned into a Lambda vector using the ZAP-Express™ vector kit (predigested with BamH1 and alkaline phosphatase treated) and the Gigapak® III Gold packaging extract (Stratagene, Amsterdam, The Netherlands) following the manufacturer's protocol. The primary libraries were amplified as per protocol by plating aliquots containing ~5×$10^4$ pfu with host E. coli strain XL1-Blue MRF' on 150 mm Petri dishes and eluting the phage in buffer. Amplified libraries were stored in 7% v/v dimethyl sulphoxide at −80° C. after freezing in liquid nitrogen. The total primary titre was 1.8×$10^6$ pfu and after amplification 6.8×$10^9$ pfu ml$^{-1}$.

Assessment of Library Quality

The phagemid vector pBK-CMV was excised from the Lambda ZAP library using ExAssist helper phage (Stratagene) as described by the manufacturer, and used to infect E. coli strain XLOLR. Plasmid-containing clones were isolated by plating on Luria-Bertani (LB) agar containing 50 μg ml$^{-1}$ kanamycin. Blue:white screening in the presence of Xgal [5-bromo-4-chloro-3-indoyl-β-D-galactoside] and IPTG [isopropylthio-β-D-galactoside] was used to determine cloning efficiency. If no DNA has been cloned into the Lambda vector, the β-galactosidase gene is expressed in the presence of the inducer IPTG, resulting in cleavage of the substrate analogue Xgal to produce a blue pigment in the colony. If however a fragment of the genomic DNA has been successfully cloned into the Lambda vector it disrupts the gene so that no enzyme is produced and the colony remains white. The ratio of blue to white colonies therefore can be used to calculate the percentage of clones containing an insert. For this library the blue:white screen gave a ratio of 7 blue to 286 white colonies, indicating that 97% of the clones contained an insert of the genomic DNA. Twenty four colonies were selected at random and plasmid DNA prepared using the Wizard®Plus SV Miniprep DNA purification system (Promega UK, Southampton) Restriction analysis using Pst1 and HindIII which flank the BamH1 cloning site followed by agarose gel electrophoresis was used to determine insert sizes. One clone out of the 24 was found to have no detectable insert. The rest had inserts ranging from 1.5 kb to 8.0 kb.

Example 3

Library Screening for Cellulases

DNA libraries in the pBK-CMV phagemid were screened for cellulase activity in a plate assay of the *E. coli* clones. To detect cellulase activity the genomic libraries were plated on LB agar containing kanamycin, 0.5% w/v carboxymethylcellulose (low viscosity sodium salt; Sigma, Poole, UK) and IPTG (15 µl of a 0.5 M solution spread on the surface of the agar in a 7 cm diameter Petri dish). Following overnight growth at 37° C., the colonies were overlayed with 3 ml molten 0.7% w/v agarose dissolved in water which had been cooled to 50° C. After this had set, the plates were flooded with 0.1% w/v Congo Red solution for 30 minutes followed by 2 washes with 1 M NaCl. Positive clones exhibiting extracellular cellulase activity were surrounded by a yellow halo against a red background (R. Teather and P. J. Wood, Applied & Environmental Microbiology, 43: 770-780, 1982).

The screening of 110,000 *E. coli* pBK-CMV clones yielded 4 zones of clearing indicating potential cellullase-producing colonies. Three of these were successfully recovered as cellulase-producing clones after homogenising the agar plug removed from the cleared zone, streaking out for single colonies and confirming the phenotype by the Congo Red test.

Example 4

Characterisation of a Cellulase-Positive Clone

Plasmid DNA was isolated from the three cellulase positive clones, and the size of the inserts determined by restriction digestion as described above. All three had the same size (about 3.5 kb) and the same size fragments after digestion as determined by gel electrophoresis. This indicated that all three isolates were identical, derived by amplification of a single clone. This was confirmed by the first round of sequencing of the plasmid DNA (using primer sites in the pBKCMV plasmid). This was carried out by the Protein and Nucleic Acid Chemistry Laboratory at Leicester University, using the Perkin Elmer 'BigDye' terminator chemistry and the model 377 ABI automated DNA sequencer. Complete coverage of the sequence was obtained by 'primer walking' from both the 5 and 3' ends of the insert. The sequence was edited using Applied Biosystems multisequence editor Seqed™ version 1.0.3. Sequence was assembled with programmes in the GCG Wisconsin Package, version 10.2-UNIX, available at the University of Leicester. This identified an insert of environmental DNA of 3410 nucleotide bases (FIG. 1).

Example 5

Identification of the Cellulase-Gene

Possible Open Reading Frames (ORF) in the nucleotide sequence of the inserted environmental DNA of clone 029cel were identified using the ORF Find facility of the MapDraw program (DNASTAR, Brighton, Mass., USA) or ORF Search from the Vector NTI Suite of programs (InforMax®, North Bethesda, Md., USA).

This identified an ORF composed of 1746 nucleotides corresponding to a protein of 581 amino acids, starting at position 3004 of the insert sequence and ending at position 1259. The sequence of this ORF was excised using EditSeq (DNASTAR) and examined by BLAST programs.

The nucleotide sequence of this ORF is shown in FIG. 2.

An examination of the nucleotide sequence using the BLASTn program, which compares a nucleotide query sequence against a non-redundant nucleotide sequence database, indicated no significant similarity to any known sequence.

An examination of the nucleotide sequence using the BLASTx program, which compares the six-frame conceptual translation products of a nucleotide query sequence (both strands) against a protein sequence database, revealed surprisingly, very low similarity (no more than 29%) to a number of bacterial endocellulases. The highest alignment score revealed 25% identity (132 amino acids) to a 527 amino acid region of CelJ, an enzyme comprising 1601 amino acids, the largest catalytic component of the cellulosome of *Clostridium thermocellum* (protein id BM1207070.1, accession D83704.1). It is very probable that an enzyme with homology this low would not have been detected using convention methods using DNA probes based on known cellulase gene sequences, especially given the very high diversity of cellulases already characterised.

The translated protein composed of 581 amino acids is shown in FIG. 3.

Example 6

Enzyme Characterization

Influence of Salt

Cells of *E. coli* pBK-CMV containing the 029cel gene are suspended in 5 ml buffer (20 mM TRIS-HCl, pH8.0; 500 mM NaCl; 0.1 mM EDTA; 0.1% Triton X-100) and disrupted by sonication on ice. The sonicated extracts are examined by agar diffusion assay on carboxymethylcellulose (CMC) at different NaCl concentrations. Sonicated extracts (100 µL) and 1 in 10 dilutions are placed in wells punched in CMC-agar plates containing varying amounts of NaCl. The plates are incubated at 37° C. for 16 hours and the resulting clearing zones indicating cellulose hydrolysis measured in millimetres. The cellulase 029cel is active over the range 0-25% w/v NaCl, although the activity at 25% w/v NaCl is lower than the activity at 0% NaCl.

Influence of pH

The influence of pH on cellulase activity is investigated using the pH-gradient plate method described by Grant & Tindall (Isolation of alkaliphilic bacteria, In: Microbial Growth and Survival in Extreme Environments, Academic Press, London, 1980, pp. 27-36). An agar medium containing CMC is poured to a depth of 1 cm in square Petri dishes and allowed to set. A uniform trough 1 cm wide is cut from one edge of the plate and agar containing 20% w/v $Na_2CO_3.10H_2O$ and 0.2 M NaOH (prepared by mixing equal volumes of sterile 0.4 M NaOH/40% w/v $Na_2CO_3.10H_2O$ and 4% w/v agar at 60° C.) is poured into the trough. The plates are developed at 37° C. overnight to allow a uniform gradient from pH 12 to pH 7 to form. To test the pH tolerance of the 029cel cellulase a narrow trough is cut through the (agar) gradient at right angles to the original trough and filled with 1 ml of sonicated cell extract. The plates were allowed to develop overnight at 37° C. The plates are treated with Congo Red for 30 minutes to visualize the zone of cellulose hydrolysis. The results indicate that the 029cel cellulase is active to about pH 11.5.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of producing ethanol, said method comprising the steps of: (a) contacting a biomass composition with an enzymatic composition comprising a polypeptide having at least 95% sequence identity to the amino acid sequence of SEQ ID NO:3 having cellulose activity to yield a sugar solution; (b) adding to the sugar solution a fermentative microorganism; and (c) culturing the fermentative microorganism under conditions sufficient to produce ethanol.

2. The method of claim 1, wherein said polypeptide has at least 97% sequence identity to the amino acid sequence of SEQ ID NO:3.

3. The method of claim 1, wherein said polypeptide has the amino acid sequence of SEQ ID NO:3.

4. The method of claim 1, wherein said method further comprises recovering said ethanol.

* * * * *

SEQUENCE LISTING

<160> NUMBER OF SEQ ID NOS: 3

<210> SEQ ID NO 1
<211> LENGTH: 3410
<212> TYPE: DNA
<213> ORGANISM: Bacillus sp.
<220> FEATURE:
<221> NAME/KEY: misc_feature
<222> LOCATION: (1)...(3410)
<223> OTHER INFORMATION: isolated from environmental sample from
      Sonachi Lake, Kenya

<400> SEQUENCE: 1

| | | | | | |
|---|---|---|---|---|---|
| atcaacacgc | tggaaagtaa | tttcaagggt | aaggccatcg | gttgccgccg | gggtagaaat | 60 |
| gtgcggttgg | atttcgttga | gcggcgtcgc | cggcgttcca | ccgagggcat | agcgcagcag | 120 |
| gttggcgatg | ccaccggtga | ggccttcggg | gccgcctacg | atgttgtgct | cagccgccca | 180 |
| tgcgatgtag | ccgtccggct | cgggttcgct | cgcggggtg | aagaagacaa | tgtcgtcgag | 240 |
| ataaggttg | ccgcttccgc | tctcaacgcc | gccgaggttg | aattggattt | cgcaaattct | 300 |
| cgttaggtcc | agcacggaat | cgccgacgag | gtcggctatg | ggaatctgaa | tgcgcccata | 360 |
| gggttgggta | cgcggaaggg | acacgtaggg | acccactttg | tcattgggcg | agacgagccg | 420 |
| gacaaagatt | tggtgcgccg | cctgcgaggg | gccttggagg | gcgagagaaa | ggtacgtgag | 480 |
| ggcgctgatg | tcgtgcgtgg | gaccgtctcc | ccagttgtcg | agattgagcc | caaatccggc | 540 |
| ccaccatccg | gcgatagtgt | agctccaatg | gtagtgacgc | tcaccctcga | agccgccgct | 600 |
| ggagagttcc | tgcaagccgt | cgccccaaat | gcccgtgatg | agcgttgcct | cgtcacggta | 660 |
| gatcacaagt | tcggcggcgg | gtgccggggg | aagatcgcct | tgagtgatca | cgagagtggc | 720 |
| ggtggcgctg | ccttcgtgat | tagggtcggt | aatggtggcg | acgaccgtgt | agctaccggg | 780 |
| ccccactggc | gcatgggtgg | aaccgttgta | ggtaaaggag | acgtcaagcc | ccacgggatg | 840 |
| ggtctcggca | agagcggcct | tggggtgcc | gtcgaaaacg | tgttccaaat | tggagagcgt | 900 |
| gatggtggcg | ggtgccttga | gcacagtcac | agaaacagtg | gattgcacgg | gatcgtgcgc | 960 |
| tgccgtgtct | gcaggtgtga | agaccacgct | gtaaaaacgg | gttccggcgg | acggtgcaag | 1020 |
| gccggacagg | acaaaggcaa | agtcgccggg | gacggcggct | actccgccgc | tcaggccggc | 1080 |
| ctccgcaagg | gtttgcccga | aggtgatggg | tgcggctgtg | ggccacatct | ccacaaggcc | 1140 |
| ggtgtccccc | tcgtcacgca | ccggcatgag | ggcggagagg | atgaatgt | aactggcttg | 1200 |
| gtaattgatg | tcgggctcgg | tgatttccca | tgagttctcc | ggccaaaaac | cattccaatc | 1260 |
| aaggtaggct | ttttgcacgg | gttggtctcg | gatcgcctga | atgcttccgc | tgtatttggg | 1320 |
| cattgggacc | cgcccgaaag | aaaaccagga | gcgggaccgt | agagtgaagt | gagggcattg | 1380 |
| tcccagtccg | gccatcgcgg | aaccaatggt | ggtagatttc | attggctgca | cggtcagcgc | 1440 |
| cgctggcata | catgttgcta | agatagacca | tgcccattgg | gttcactccg | tggagatagt | 1500 |
| gcaggtagcc | catcgcggca | tcgcgatgcg | cggccgcgtc | ggcggggttg | agcccaagcc | 1560 |
| tccgtacccc | ctcgaagaaa | aagccagcct | gagactttgt | tttgttcgag | ccccacgtgt | 1620 |

```
aatcctgatc cttcaggtag gcgcggtagg cgtcggtctg gttattccat gcaccgagaa    1680
actccccacc gtttatagaa gccgccatcc ggttgcggat gtcggcagag acgctaggcg    1740
tcgctcccgg gagggtcgtg tagtgggcga gagcttttg tagctcacct tgaaagggga    1800
agaaatacca ccactgcacg ggctccatat cgagatagcg cacatcgaag aaatcgcgat    1860
agaccgcacc gcccgtgcgc tcgaagagca tggcggcggc catcacacgg ttggctagcg    1920
tatcgtgggc attgcgcgag gggctcacgg aagcaaatcc ggtgttgtcg aaaggcacat    1980
gaggatggac catggtccaa ttccatgcgg cgatggcagc ggattcgagg gtgacggcat    2040
aatcgctcat gcctacgctc tcaaagacag tcgccccgag ggcgaaagcg gcggcagcca    2100
tggcagtggc ctcggtcgag acggggccgt agtaacgcgg atgggtgtcg gtgctcggcg    2160
ggctggcgct ctggtgcccc gtcacggaaa ctttcccgag aatagccccg ctcggctcct    2220
gcatgcgtaa gagccagtcc attccccatt tgacttcgtc aagcaggtcg gggacaccgt    2280
tgccggattc cggatgcca aaatcatcgg taaagacgtc aggccgccct tgataggcaa    2340
ggagcagctc caggatgacg cgccccgtcc actcgctgta cttgttgaaa tcgcccgcat    2400
cgaaccaacc gccgctgaga tcgcgctcca aggaggcatt ccccatatcc cagatggggc    2460
ggctggcgac gtcctgcggg tgagaagcgg catcggccca gttcgcgtgg gcgtagggca    2520
cctccttggc aaacccggag cgctgataga agaacatgcg cacggcctcg cgcaggacaa    2580
catcgtaaac atccgcgcca atggcgaaac tatcggaatg agtgttgttg gcaggatcgt    2640
ggatgcggta gtggccgggc tcggcaacta ccgtaaaatc aaaccaccac acgcggtctc    2700
ccgattgaat atggatggcg ccgccgttcc acggaccgg tgagccggag aaaaccacga    2760
cgccatcgtt cacgcgacgg acctccagcg ttgcgccggg gctgtagctc tcggcgctgt    2820
tccagccaat ctgcgggtcg cgatcaccg ccaccttggt ggcatcggcg gggtaaccga    2880
attggtcgat gcggatttta tcggtgtggg tggaggcgac gagggcggag ctgcccatga    2940
gcagcaagaa aaagcccgct gtcggcccga taccaaaaaa acgaataggg agagaaaaat    3000
tcatagcagg atgtggatac ggaaaggggg aaaacggtgc aaagacccaa gcccaacgct    3060
tggcgaaaac tggatggttg gtttatcaag aaaagcgctt ttgagccaaa agctgcgggc    3120
aatccttatt gcgtttcaca atattttcac atcgtcggcg gcacgacttt tcgatgggcg    3180
acttgacagc gtattctctc aggcgcgagg ctgcaaacct tatgaaaaaa ggcccgcgca    3240
gcgatctgtc cccggtcaaa atccagtcaa ggtttgttca agggtttgag gtctgataga    3300
ggcacagtcg agccatcagc agtcgcattg agtagggttg ttggagaaag tgtgcaaatg    3360
accgctgccg aaggaactgt ggagacaaaa agcatatttt cctcgccaag                3410
```

<210> SEQ ID NO 2
<211> LENGTH: 1746
<212> TYPE: DNA
<213> ORGANISM: Bacillus sp.
<220> FEATURE:
<221> NAME/KEY: misc_feature
<222> LOCATION: (1)...(1746)
<223> OTHER INFORMATION: isolated from environmental sample from
      Sonachi Lake, Kenya

<400> SEQUENCE: 2

```
atgaattttt ctctccctat tcgttttttt ggtatcgggc cgacagcggg ctttttcttg      60
ctgctcatgg gcagctccgc cctcgtcgcc tccacccaca ccgataaaat ccgcatcgac     120
caattcggtt accccgccga tgccaccaag gtggcggtga tcgccgaccc gcagattggc     180
tggaacagcg ccgagagcta cagccccggc gcaacgctgg aggtccgtcg cgtgaacgat     240
```

```
ggcgtcgtgg ttttctccgg ctcaccggtc ccgtggaacg gcggcgccat ccatattcaa    300
tcgggagacc gcgtgtggtg gtttgatttt acggtagttg ccgagcccgg ccactaccgc    360
atccacgatc ctgccaacaa cactcattcc gatagtttcg ccattggcgc ggatgtttac    420
gatgttgtcc tgcgcgaggc cgtgcgcatg ttcttctatc agcgctccgg gtttgccaag    480
gaggtgccct acgccacgc gaactgggcc gatgccgctt ctcacccgca ggacgtcgcc    540
agccgcccca tctgggatat ggggaatgcc tccttggagc gcgatctcag cggcggttgg    600
ttcgatgcgg gcgatttcaa caagtacagc gagtggacgg ggcgcgtcat cctggagctg    660
ctccttgcct atcaagggcg gcctgacgtc tttaccgatg attttggcat cccggaatcc    720
ggcaacggtg tccccgacct gcttgacgaa gtcaaatggg gaatggactg gctcttacgc    780
atgcaggagc cgagcggggc tattctcggg aaagtttccg tgacggggca ccagagcgcc    840
agcccgccga gcaccgacac ccatccgcgt tactacggcc ccgtctcgac cgaggccact    900
gccatggctg ccgccgcttt cgccctcggg gcgactgtct tgagagcgt aggcatgagc    960 gattatgccg tcaccctcga atccgctgcc atcgccgcat ggaattggac catggtccat   1020
cctcatgtgc ctttcgacaa caccggattt gcttccgtga gcccctcgcg caatgcccac   1080
gatacgctag ccaaccgtgt gatggccgcc gccatgctct tcgagcgcac gggcggtgcg   1140
gtctatcgcg atttcttcga tgtgcgctat ctcgatatgg agcccgtgca gtggtggtat   1200
ttcttcccct ttcaaggtga gctacaaaaa gctctcgccc actacacgac cctcccggga   1260
gcgacgccta gcgtctctgc cgacatccgc aaccggatgg cggcttctat aaacggtggg   1320
gagtttctcg gtgcatggaa taaccagacc gacgcctacc gcgcctacct gaaggatcag   1380
gattacacgt ggggctcgaa caaaacaaag tctcaggctg gcttttctt cgaggggta    1440 cggaggcttg ggctcaaccc cgccgacgcg gccgcgcatc gcgatgccgc gatgggctac   1500
ctgcactatc tccacggagt gaacccaatg ggcatggtct atcttagcaa catgtatgcc   1560
agcggcgctg accgtgcagc caatgaaatc taccaccatt ggttccgcga tggccggact   1620
gggacaatgc cctcacttca ctctacggtc ccgtcctgg ttttctttcg ggcgggtccc    1680
aatgcccaaa tacagcggaa gcattcaggc gatccgagac caacccgtgc aaaaagccta   1740
ccttga                                                              1746
```

<210> SEQ ID NO 3
<211> LENGTH: 581
<212> TYPE: PRT
<213> ORGANISM: Bacillus sp.
<220> FEATURE:
<221> NAME/KEY: VARIANT
<222> LOCATION: (1)...(581)
<223> OTHER INFORMATION: isolated from environmental sample from Sonachi Lake, Kenya

<400> SEQUENCE: 3

```
Met Asn Phe Ser Leu Pro Ile Arg Phe Phe Gly Ile Gly Pro Thr Ala
 1               5                  10                  15

Gly Phe Phe Leu Leu Leu Met Gly Ser Ser Ala Leu Val Ala Ser Thr
            20                  25                  30

His Thr Asp Lys Ile Arg Ile Asp Gln Phe Gly Tyr Pro Ala Asp Ala
        35                  40                  45

Thr Lys Val Ala Val Ile Ala Asp Pro Gln Ile Gly Trp Asn Ser Ala
    50                  55                  60

Glu Ser Tyr Ser Pro Gly Ala Thr Leu Glu Val Arg Arg Val Asn Asp
65                  70                  75                  80
```

```
Gly Val Val Val Phe Ser Gly Ser Pro Val Pro Trp Asn Gly Ala
                85                  90                  95
Ile His Ile Gln Ser Gly Asp Arg Val Trp Trp Phe Asp Phe Thr Val
            100                 105                 110
Val Ala Glu Pro Gly His Tyr Arg Ile His Asp Pro Ala Asn Asn Thr
            115                 120                 125
His Ser Asp Ser Phe Ala Ile Gly Ala Asp Val Tyr Asp Val Val Leu
130                 135                 140
Arg Glu Ala Val Arg Met Phe Phe Tyr Gln Arg Ser Gly Phe Ala Lys
145                 150                 155                 160
Glu Val Pro Tyr Ala His Ala Asn Trp Ala Asp Ala Ser His Pro
                165                 170                 175
Gln Asp Val Ala Ser Arg Pro Ile Trp Asp Met Gly Asn Ala Ser Leu
            180                 185                 190
Glu Arg Asp Leu Ser Gly Gly Trp Phe Asp Ala Gly Asp Phe Asn Lys
            195                 200                 205
Tyr Ser Glu Trp Thr Gly Arg Val Ile Leu Glu Leu Leu Ala Tyr
    210                 215                 220
Gln Gly Arg Pro Asp Val Phe Thr Asp Asp Phe Gly Ile Pro Glu Ser
225                 230                 235                 240
Gly Asn Gly Val Pro Asp Leu Leu Asp Glu Val Lys Trp Gly Met Asp
            245                 250                 255
Trp Leu Leu Arg Met Gln Glu Pro Ser Gly Ala Ile Leu Gly Lys Val
            260                 265                 270
Ser Val Thr Gly His Gln Ser Ala Ser Pro Pro Ser Thr Asp Thr His
    275                 280                 285
Pro Arg Tyr Tyr Gly Pro Val Ser Thr Glu Ala Thr Ala Met Ala Ala
    290                 295                 300
Ala Ala Phe Ala Leu Gly Ala Thr Val Phe Glu Ser Val Gly Met Ser
305                 310                 315                 320
Asp Tyr Ala Val Thr Leu Glu Ser Ala Ala Ile Ala Ala Trp Asn Trp
            325                 330                 335
Thr Met Val His Pro His Val Pro Phe Asp Asn Thr Gly Phe Ala Ser
            340                 345                 350
Val Ser Pro Ser Arg Asn Ala His Asp Thr Leu Ala Asn Arg Val Met
    355                 360                 365
Ala Ala Ala Met Leu Phe Glu Arg Thr Gly Gly Ala Val Tyr Arg Asp
370                 375                 380
Phe Phe Asp Val Arg Tyr Leu Asp Met Glu Pro Val Gln Trp Trp Tyr
385                 390                 395                 400
Phe Phe Pro Phe Gln Gly Glu Leu Gln Lys Ala Leu Ala His Tyr Thr
                405                 410                 415
Thr Leu Pro Gly Ala Thr Pro Ser Val Ser Ala Asp Ile Arg Asn Arg
            420                 425                 430
Met Ala Ala Ser Ile Asn Gly Gly Glu Phe Leu Gly Ala Trp Asn Asn
            435                 440                 445
Gln Thr Asp Ala Tyr Arg Ala Tyr Leu Lys Asp Gln Asp Tyr Thr Trp
    450                 455                 460
Gly Ser Asn Lys Thr Lys Ser Gln Ala Gly Phe Phe Glu Gly Val
465                 470                 475                 480
Arg Arg Leu Gly Leu Asn Pro Ala Asp Ala Ala Ala His Arg Asp Ala
            485                 490                 495
Ala Met Gly Tyr Leu His Tyr Leu His Gly Val Asn Pro Met Gly Met
```

-continued

```
                500                     505                     510

Val Tyr Leu Ser Asn Met Tyr Ala Ser Gly Ala Asp Arg Ala Ala Asn
        515                     520                 525

Glu Ile Tyr His His Trp Phe Arg Asp Gly Arg Thr Gly Thr Met Pro
        530                     535                 540

Ser Leu His Ser Thr Val Pro Leu Leu Val Phe Phe Arg Ala Gly Pro
545                     550                     555                 560

Asn Ala Gln Ile Gln Arg Lys His Ser Gly Asp Pro Arg Pro Thr Arg
                565                     570                 575

Ala Lys Ser Leu Pro
                580
```